United States Patent [19]

Schenk

[11] Patent Number: 4,746,020

[45] Date of Patent: May 24, 1988

[54] METHOD AND AN APPARATUS FOR MARKING FAULTS ON RAPIDLY MOVING MATERIAL WEBS

[75] Inventor: Christoph Schenk, Icking, Fed. Rep. of Germany

[73] Assignee: Erwin Sick GmbH Optik-Elektronik, Waldkirch, Fed. Rep. of Germany

[21] Appl. No.: 890,796

[22] Filed: Jul. 24, 1986

Related U.S. Application Data

[63] Continuation-in-part of Ser. No. 627,385, Jul. 3, 1984, abandoned.

[30] Foreign Application Priority Data

Jul. 12, 1983 [DE] Fed. Rep. of Germany ....... 3325125

[51] Int. Cl.$^4$ .................. B07C 5/342; B05C 11/00
[52] U.S. Cl. .................................... 209/3.3; 83/362; 118/670; 209/564; 209/587; 226/45; 356/431; 364/507
[58] Field of Search ................................ 209/3.1–3.3, 209/559, 562–566, 576, 577, 578, 579, 587; 83/27, 72, 80, 89, 106, 360, 362, 365; 118/665, 669, 670, 675; 250/562, 563; 356/429–431, 238; 364/475, 507; 377/17, 18, 20, 39, 54

[56] References Cited

U.S. PATENT DOCUMENTS

| | | | |
|---|---|---|---|
| 2,758,712 | 8/1956 | Linderman | 209/3.3 X |
| 3,290,167 | 12/1966 | Wood et al. | 118/670 X |
| 3,793,983 | 2/1974 | Shelestak | 118/670 |
| 4,004,904 | 1/1977 | Fergusson | 377/54 X |
| 4,073,260 | 2/1978 | Bosworth et al. | 118/670 |
| 4,134,684 | 1/1979 | Jette | 356/430 |
| 4,166,541 | 9/1979 | Smith, Jr. | 209/587 |
| 4,211,132 | 7/1980 | Nichols, III et al. | 209/576 X |
| 4,395,764 | 7/1983 | Matsue | 377/54 X |
| 4,507,564 | 3/1985 | Shimada | 356/431 X |

FOREIGN PATENT DOCUMENTS 1773279 9/1971 Fed. Rep. of Germany.
2850203 5/1979 Fed. Rep. of Germany.

Primary Examiner—Robert R. Reeves
Assistant Examiner—Edward M. Wacyra
Attorney, Agent, or Firm—Townsend and Townsend

[57] ABSTRACT

In a method of marking faults on rapidly moving material webs the material web is moved past a fault detection scanning device, which cyclically scans the web transverse to its longitudinal direction, and past a marking device at a defined distance therefrom. Signals coming from the fault detection scanning device (16) are analyzed one after the other to determine whether they are fault signals or structure signals. The fault signals which are detected are stored with their web coordinates. Checks are made at short time intervals as to whether a fault signal is present in the store (11) which corresponds to the longitudinal coordinate which is just moving past the marking device (13). A marking is effected if a fault signal is present at the corresponding web coordinates (FIG. 1).

8 Claims, 1 Drawing Sheet

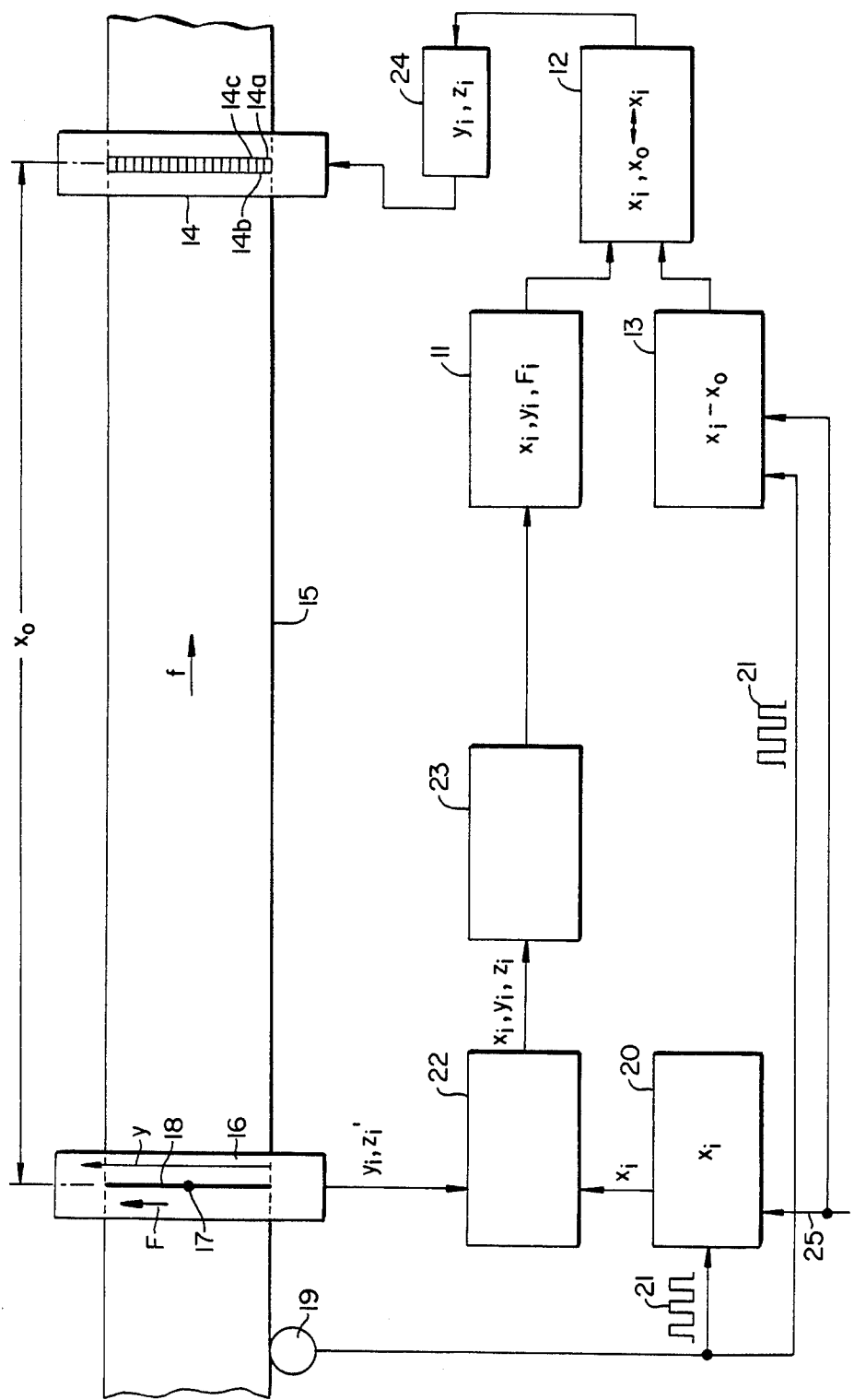

METHOD AND AN APPARATUS FOR MARKING FAULTS ON RAPIDLY MOVING MATERIAL WEBS

This is a continuation-in-part of application Ser. No. 627,385, filed 07/03/84, now abandoned.

The invention relates to an arrangement for marking faults on rapidly moving material webs or for sorting out faulty pieces of material, the apparatus comprising a fault detection scanning device for cyclically scanning a web transverse to its longitudinal direction to detect faults and generate fault signals, a memory for storing fault signals, and a marking or sorting device provided at a defined distance from the fault detection scanning device, wherein the marking or sorting device makes an appropriate mark on the web, or sorts out an appropriate part of the web, in dependence on the presence of a fault signal at specific coordinates of the web.

During surface inspection material webs, for example magnetic foils, are continuously moved in their longitudinal direction and relatively rapidly past a fault detection scanning device. The fault detection scanning device generally operates with a laser beam, which is cyclically guided transversely over the web by a mirror wheel, and with a light receiver which transmits different electrical signals to an electronic processing circuit, depending on whether or not the point of the web just scanned by the laser beam exhibits a fault or not. Such fault detection scanning devices are known in many variations.

Frequently it is not sufficient during surface inspection merely to detect a fault, instead a mark should often be made at the detected position of the fault. For this purpose a marking device can be provided spaced apart from the fault detection scanning device, and indeed transversely to the direction of movement of the web, below or above the web. Colour sprays, marking pens, labelling devices, magnetic heads and the like are suitable for effecting the marking, depending on the type of marking that is desired and on the type of marking that is possible with the material to be monitored.

By way of example, the use of magnetic heads can be considered during the surface inspection of magnetic tapes. Such magnetic tapes, which are used for the manufacture of audio or video tapes, are manufactured in relatively large widths of for example 700 mm. In this case it is expedient to arrange approximately 120 magnetic heads directly alongside one another over the width of the web by means of which faults can be magnetically marked in a relatively fine raster.

As a rule it is not possible to arrange the marking device at the same location as the fault detection scanning device. The marking device is therefore arranged displaced by a certain distance in the direction of movement of the web after the fault detection scanning device. The fault information delivered by the fault detection scanning device can be delayed timewise with the aid of a shift register in such a way that the marking can in each case take place at the location of the fault. If one selects the clock frequency of the register so that it is proportional to the speed of the web then the marking device will be activated at the instance at which the fault passes the marking device. The number of clock pulses which elapse between the fault passing the fault detection scanning device and the marking device determines the length of the shift register.

It is a precondition for the troublefree operation of this method that the fault signal is fed into the shift register within a very short time after the fault has been detected. The delay time should be smaller than one clock period. The speed of advance is determined by an incremental transducer controlled by the web feed. In this way the feed of the web is digitised in that the feed is for example subdivided into individual steps of 1 mm for example. In other words fault detection is effected by scanning the web after each 1 mm of feed.

The fault detection scanning device does not generally transmit fault signals which can be straightforwardly evaluated. On the one hand the fault signals are very diverse, depending on the nature of the fault (hole, scratch, dent etc.); on the other hand, even the faultfree structure of the web frequently leads to signals which can only be distinguished with difficulty from true fault signals. By way of example one finds very many holes in textile webs which belong to the normal structure of the relevant web material. These holes however initiate many hole signals when using a fault detection scanning device which responds to the presence of holes, and these fault signals have to be distinguished from true fault signals which, for example, occur if a warp thread is missing in the web material.

A complicated analysis procedure is generally necessary to separate true fault signals from structure signals which do not represent faults. For rapidly moving material webs with many faulty regions the data rate can be too high for the continuous and instant processing of the signals. One could indeed use a buffer store for speed matching with the delay time in the buffer store being dependent on the degree of filling. However, the computing time of an evaluation computer that may be used can also vary depending on the ingoing data. This signifies that the time between the passage of a fault through the fault detection scanning device and the recognition of the fault is firstly very large and secondly variable. For this reason accurate fault marking in the transport direction is no longer possible.

Furthermore, it is also already known from German Offenlegungsschrift DE-OS No. 17 73 279 to arrange several pieces of apparatus which respond to different faults one after the other in the transport direction along a track, with the pieces of apparatus being connected to an electronic processing circuit in order to initiate the sorting out of damaged goods. In this known apparatus any fault which occurs has to be recognised, i.e. analysed, while the fault is passing the apparatus. There is thus likewise no time available for carrying out a complicated analysis to distinguish between structural and fault signals.

A complete surface inspection system is also already known, from German Offenlegungsschrift DE-OS No. 28 50 203, for the sorting out of faulty sheet material, for example the sheets of an X-ray film. In this known surface inspection system the evaluation of the received signals also has to take place immediately, i.e. while the material is passing through the scanning apparatus.

When compared with this prior art the object underlying the invention is to provide an arrangement of the initially named kind by means of which a troublefree and ordered marking of the web, or sorting out of faulty parts of the web, is possible at a defined distance from the fault detection scanning device with relatively low complexity, even with material webs which are running or advanced at high speed, and with very complicated fault and structure signals being delivered by the fault detection scanning device which require a lot time for analysis.

In order to satisfy this object the invention provides that the fault detection scanning device is connected to a fault signal analyser which examines the ingoing signals, independently of the speed of the web, solely in dependence on the time required for any particular signal, to establish whether the signals are fault signals or structure signals, and then delivers the fault signals which are found to the fault signal memory which stores the web coordinates of the fault signals, likewise independently of the speed of advance of the web; that the fault signal memory is connected to a comparator; that a longitudinal coordinate counter is also connected to the comparator, said comparator checking at short time intervals whether a fault signal is present in the fault signal memory in respect of each longitudinal coordinate, which it receives from the longitudinal coordinate counter at the moment the corresponding coordinate moves past the marking or sorting device; and that, on detecting a corresponding fault signal, the comparator transmits a marking or sorting signal to the marking or sorting device.

As a result of this arrangement the fault signals detected during the fault analysis are analysed completely independently of the speed of the web, solely in accordance with the time required for a special signal, and are likewise temporarily stored totally independently of the feed of the web. Only when a point of the web for which a fault has already been detected reaches the marking device is the content of the store checked to see whether fault signals are or are not stored for the associated longitudinal coordinate. If fault signals are stored then these fault signals are extracted from the store and used to make an appropriate mark on the web.

In order to keep the capacity of the store as small as possible the relevant fault signal in the store should be erased after finding a fault signal at specific web coordinates.

In order to make marking of the web possible not only in a longitudinal direction but also in the transverse direction a particularly preferred embodiment envisages, that a marking device is provided, that the marking device has a plurality of markers arranged transverse to the longitudinal direction of the web, that the fault signal memory also stores the transverse coordinate of each fault signal, and that signals transmitted from the comparator to the marking device also contain a transverse coordinate component.

The rapidly operating fault signal store thus registers not only the fault signals but also their coordinates in the direction of feed and transverse to the direction of feed of the material web. The fault signal itself can have different values depending on the character of the fault that is found. In the fault analyser the type of fault and the location of the fault are determined in absolute coordinates.

At the start of the inspection a feed coordinate counter, which may for example be controlled by an incremental transducer and which is located at the fault detection scanning device, is set to zero. Simultaneously a corresponding feed coordinate counter of the marking device is set to a negative value corresponding to the spacing of the two devices. The instantaneously valid feed coordinate at the marking device is now compared with the feed coordinate of the already stored fault signals at short feed intervals of 1 mm for example. If the two values correspond within a preselected tolerance then a marking procedure is initiated.

In this way it is possible to mark the errors on the web with high accuracy in the feed direction. By arranging a plurality of markers transverse to the transport direction it is also possible, by evaluating the transverse coordinate, to mark the fault in the transverse direction. The resolution of the marking in the transverse direction is determined by the number of markers which are used. For lower speed it is also possible to displace the marking head in the transverse direction in accordance with the specified coordinate.

As a result of the comparison which takes place at the marking device, of the absolute coordinate with the stored coordinates, the fault marking in the direction of feed is independent of the time which is required for the fault analysis. The only condition is that the time at which the material web is transported from the inspection location to the marking location should be greater, at the highest speed of the web, than the maximum time required for the fault analysis. This condition can be straightforwardly satisfied by selecting a suitable spacing.

The invention will now be described in the following by way of example and with reference to the drawing the single FIGURE of which shows a schematic reproduction of an arrangement for marking faults on rapidly advanced material webs.

As seen in the drawing a material web 15 shown in plan view is advanced in the direction of the arrow f with a predetermined speed of for example 10 m/s.

A fault detection scanning device 16 is provided at a specific position of the web 15 either above or below it. The fault detection scanning device 16 develops a bead of light on the web 17 which is cyclically guided over the web in the direction of the arrow F, which results in a schematically illustrated line of light 18.

An incremental transducer 19 is also arranged in the vicinity of the fault detection scanning device 16. The incremental transducer transmits a signal which corresponds to the feed of the web 15 and controls a feed coordinate counter. The incremental transducer transmits a clock signal which causes the subsequent circuit to process the faults at specified time intervals corresponding for example to a feed of the web of 1 mm.

The feed frequency 21 delivered by the incremental transducer 19 is applied, on the one hand, to the longitudinal coordinate counter 20 associated with the fault detection scanning device 16 and, on the other hand, to a second longitudinal coordinate counter 13 associated with the marking device 14. The marking device is arranged at a distance $x_O$ in the direction of movement f after the fault detection scanning device 16 and extends transversely across the web 15 either above it or below it. The marking device 14 consists of numerous markers $14a$, $14b$, $14c$, . . . which lie alongside one another in the transverse direction and which make it possible to apply an optical, electrical or magnetic marking to the web 15 at the relevant location at a desired time.

The longitudinal coordinate counter 20 is applied to a fault signal analyzer 22 to which the signals $z'_i$ received by the scanning device 16 together with the associated coordinate $y_i$ where the respective signal $z'_i$ was received, is also passed. y is the coordinate indicated in the drawing of a specific point of the web at the location of the line of light 18 in the transverse direction of the web.

In the fualt signal analyzer 22 it is decided for each longitudinal coordinate $x_i$ whether the received signal $z'_i$ is a normal structural signal or a fault signal $z_i$. If a fault signal $z_i$ has been detected it is also determined, at which transverse coordinate $y_i$ the fault signal was received. Only fault signals $z_i$ are transferred to the following output registe 23. The structural signals are suppressed in the analyzer 22. The fault signal $z_i$ can have different values depending n the type of fault that is found by the fault analyzer 22.

The fault signal analyzer 22 receives and stores all the scanned signals $z_i'$ as the respective signals occur. The decision process in the analyzer 22, during which the decision is made whether the received signal $z_i'$ has originated from the normal structure of the web or from a fault, and during which the fault is classified by type of fault $z_i$, is accomplished independently of the time within which the signals $z_i'$ are received by the analyzer 22. A fault signal forms a fault word from the values $x_i$, $y_i$ and $z_i$. In the fault signal store 11 the fault signals which are found are stored in dependence on the type of fault $z_i$ and also its web coordinate $x_i$, $y_i$. The serial by word transfer from the output register 23 to the fault signal store 11 can take place as desired either serial by bit or parallel by bit.

A comparator 12 is connected to the store 11. The output signal from the second longitudinal coordinate counter 13 is passed to the other input of the comparator. The comparator 12 compares the longitudinal coordinate signal transmitted by the longitudinal coordinate counter 13 with the content of the store 11 and transmits an output signal as soon as a fault signal is stored for a particular longitudinal coordinate $x_i$ in the store 11. The corresponding marking signal is transmitted via an output register 24 to the marking device and energizes, in dependence on the transverse coordinate $y_i$, the associated marker 14a, 14b, 14c with the fault signal $z_i$.

As the second longitudinal coordinate counter 13 transmits its coordinate signal to the comparator 12 with the delay $x_O/v$, where v is the speed of the web, the markers 14a, 14b, 14c are actuated, if a fault is present, exactly at the moment when the point of the web for which a fault signal has been determined by the fault detection scanning device 12 is located exactly beneath the marker of the marking device 14.

As a result of the arrangement of the invention the speed with which the individual fault signals are stored in the store 11 is unimportant as the required association at the marking device 14 is restored by the comparator 12 and the longitudinal coordinate counter 13. It is only necessary for all the fault signals detected by the fault detection scanning device 16 to be stored in the store 11 at the time when the relevant faults in the web reach the marking device 14 after passing along the path $x_O$.

For troublefree functioning of the arrangement of the invention it is also necessary that the comparator 12 can carry out a comparison with the content of the store 11 within one cycle.

A zero setting pulse can also be applied to the longitudinal coordinate counters 13, 20 via a line 25 in order to be able to specify the time at which fault analysis begins.

I claim:

1. An apparatus for marking faults on rapidly moving material web, or for sorting out faulty pieces of material, the apparatus comprising:
   a fault detection scanning device for cyclically scanning a web transverse to its longitudinal direction to detect potential faults and generate potential fault signals;
   a memory for storing fault signals and corresponding web coordinates;
   a marking or sorting device provided at a defined distance from the fault detection scanning device for making an appropriate mark on the web, or for sorting out an appropriate part of the web;
   a fault signal analyzer means connected to the fault detection scanning device for storing the potential fault signals, and for examining the potential fault signals independently of the speed of the web, to establish whether the potential fault signals are true fault signals or structure signals, and for then delivering the true fault signals which are found and the corresponding web coordinates to the fault signal memory, which stores the true fault signals and corresponding web coordinates, likewise independently of the speed of advance of the web;
   a comparator connected to the fault signal memory; and
   a longitudinal coordinate counter connected to the comparator;
   said comparator being operative for checking at short time intervals whether a true fault signal is present in the fault signal memory corresponding to each longitudinal coordinate, which said comparator receives from the longitudinal coordinate counter at the moment the part of the web having the corresponding longitudinal coordinate moves past the marking or sorting device and for transmitting marking or sorting signal to the marking or sorting device when a true fault signal corresponding to the longitudinal coordinate received from the longitudinal coordinate counter is present in the fault signal memory, said marking or sorting device being operatively connected to said comparator for making an appropriate mark on the web, or sorting out an appropriate part of the web, in response to the marking or sorting signal from said comparator.

2. The apparatus of claim 1, wherein said fault signal analyzer means comprises means for classifying the true fault signals according to the type of fault.

3. The apparatus of claim 2, comprising a marking device having a plurality of markers arranged transverse to the longitudinal direction of the web wherein the fault signal memory also stores the transverse coordinate of each fault signal and wherein signals transmitted from the comparator to the marking device also contain a transverse coordinate component.

4. The apparatus of claim 2, wherein on finding a fault signal at specific web coordinates in the memory the relevant fault signal in the memory is deleted.

5. A method for marking faults on rapidly moving material webs, or for sorting out faulty pieces of material, using a marking or sorting device, comprising the steps of:
   cyclically scanning a web transverse to its longitudinal direction to about potential faults and generate potential fault signals;
   storing the potential fault signals and corresponding web coordinates;
   examining the stored potential fault signals, independently of the speed of the web, to establish whether the potential fault signals are true fault signals or structure signals;

storing the true fault signals and the corresponding web coordinates;

checking, at short time intervals, to determine whether there is a stored true fault signal having a longitudinal coordinate corresponding to the longitudinal coordinate of the part of the web passing the marking or sorting device;

transmitting a marking or sorting signal to the marking or sorting device upon finding a stored true fault signal having a longitudinal coordinate corresponding to the part of the web passing the marking or sorting device; and making an appropriate mark on the web, or sorting out an appropriate part of the web, in response to the marking or sorting signal.

6. The method of claim 5 wherein the examining step includes the step of classifying the true fault signals according to the type of fault.

7. The method of claim 6 wherein the step of storing the true fault signal includes storing the transverse coordinate of each true fault signal and the transmitting step includes transmitting the transverse coordinate of each fault signal.

8. The method of claim 6 further comprising the step of deleting the stored true fault signal after the stored true fault signal is found by said checking step.

* * * * *